United States Patent [19]

Skold

[11] 4,268,663
[45] May 19, 1981

[54] MACROMOLECULAR GLYCOSIDASE SUBSTRATES

[75] Inventor: Carl N. Skold, Palo Alto, Calif.

[73] Assignee: Syva Company, Palo Alto, Calif.

[21] Appl. No.: 28,777

[22] Filed: Apr. 10, 1979

[51] Int. Cl.³ .................... C07H 15/00; C08B 37/02
[52] U.S. Cl. ............................................ 536/4; 435/7; 424/180; 536/1; 536/18; 536/112; 536/120
[58] Field of Search ................. 536/1, 18, 120, 112, 536/4

[56] References Cited

U.S. PATENT DOCUMENTS

| | | | |
|---|---|---|---|
| 3,823,100 | 7/1974 | Rothwell et al. | 536/114 |
| 4,011,205 | 8/1977 | Dean et al. | 536/1 |
| 4,012,570 | 3/1977 | Dean et al. | 536/1 |
| 4,145,527 | 3/1979 | Burns et al. | 536/1 |

Primary Examiner—Johnnie R. Brown
Attorney, Agent, or Firm—Bertram I. Rowland

[57] ABSTRACT

Macromolecular compositions are provided which find use as glycosidase substrates, particularly where steric modulation of enzyme activity is involved. The compositions have a macromolecular hub to which is linked by means of a spacer arm a chromophore, which in turn is bonded to a sugar by an enzymatically labile glycosidyl linkage. The chromophore is chosen so as to undergo a substantial change in its chromophoric properties upon cleavage of the glycosidyl linkage. The enzyme activity can be determined spectrophotometrically due to the change in the absorptive or fluorescent properties of the chromophore upon cleavage of the glycosidyl linkage. Varying turnover rates for the enzyme are observed depending upon the nature of the macromolecular hub, the spacer arm, and the chromophore.

11 Claims, No Drawings

MACROMOLECULAR GLYCOSIDASE SUBSTRATES

BACKGROUND OF THE INVENTION

1. Field of the Invention

The use of enzymes finds broad application in a wide variety of analytical techniques, such as diagnostic assays, histochemical staining, chromatographic examination, and the like. In diagnostic assays, a number of assay techniques have been developed which involve steric effects for modulating the observed signal in relation to the analyte. For the most part, steric repulsions are involved, where the substrate is inhibited from approaching the active site of the enzyme by the presence of large molecules bound to the enzyme in the vicinity of the active site.

In employing enzymes in the diagnostic assays, the enzymes are normally labeled with a ligand, so that upon binding of antiligand to ligand, the substrate is sterically excluded from the active site. In chosing an enzyme for use in diagnostic assays, there are many considerations which come into play. Among these considerations are storage stability, turnover rate, presence in fluids to be measured, susceptibility to inhibition, pH optimum, susceptibility to steric exclusion of substrate, availability, degree of characterization, and methods for determination of enzymatic activity. Therefore, different enzymes may be preferable for different assays.

The glycosidases have many desirable properties, in that many of them have high turnover rates, are stable for long periods of time, particularly when lyophilized, can be readily conjugated to other molecules, and have substrates other than their natural substrates which permit the determination of enzyme activity by spectrophotometric means. However, these reagents are monosaccharides and are therefore small and are only difficultly excluded from the enzyme active site by steric effects. In order to use these enzymes where steric exclusion is applicable for modulating the signal in relation to the amount of analyte in the assay medium, it is desirable to provide substrates which would be more readily sterically excluded from the active site.

2. Description of the Prior Art

Cuatrecasas, J. Biol. Chem., 246, 196 (1971) describes an affinity chromatography column for β-galactosidase employing β-thiogalactoside linked to an insoluble support by a dipropylenetriamine spacer arm. U.S. Pat. No. 3,817,837 describes a homogeneous enzyme immunoassay involving steric exclusion of a substrate from an enzyme. More recently, a technique involving particulate reagents is described in copending application Ser. No. 964,099 filed Nov. 24, 1978.

SUMMARY OF THE INVENTION

Macromolecular organic compositions are provided having a plurality of glycosidyl substituted chromophores linked by a spacer arm to a macromolecular hub nucleus, where the glycosidyl linkage is enzymatically labile. Upon enzymatic hydrolysis of the glycosidyl linkage, the chromogen undergoes a substantial change in its chromogenic properties. The chromogen, after removal of the glycoside substituent, may be a dye which absorbs at wavelengths greater than 300 nm or a fluorescer. Various spacer arms are employed, usually neutral or positively charged under the conditions of use. The compositions find particular use in diagnostic assays having enzyme labels, where the signal is modulated by steric exclusion of a substrate to the enzyme active site.

DESCRIPTION OF THE SPECIFIC EMBODIMENTS

Macromolecular organic compositions are provided, generally having a plurality of glycosidyl substituted chromogenic groups, with the chromogen linked to a macromolecular hub nucleus through a bond or spacer arm. The glycosidic linkages are enzymatically labile and upon cleavage of the glycosidic linkage, the chromogen undergoes a substantial change in its chromogenic properties, so that at a predetermined wavelength or wavelength range, there is a substantial change in the extinction coefficient or the compound becomes fluorescent or vice versa.

The compositions of this invention will have molecular weights of at least 10,000, and usually substantially in excess of 10,000. On the average, there will be at least one glycosidyl substituted chromogenic group per hub nucleus, usually on the average at least two per hub nucleus and generally more. The spacer arm will have at least one atom in the chain, usually at least three atoms in the chain and may have as many as 35 atoms in the chain, connecting the chromogen to the hub nucleus. (By chain is intended a connected series of atoms, which except at the terminii, are bonded to adjacent atoms on opposite sides. Where rings are involved, the shortest series of atoms between the atoms bonded to the atoms of the chain or a substituent at the end of the chain. The atoms of the chain are at least divalent, forming stable covalent bonds.) Depending upon the nature of the hub nucleus and the available functionalities for linking present on the hub nucleus and the chromogen, the linking group can vary widely as to the particular functionality involved in joining the chromogen to the hub nucleus.

The compositions of the subject invention may be divided into four constituent parts: (1) the macromolecular hub nucleus; (2) the spacer arm; (3) the chromogen; and (4) the monosaccharide. Each of these elements will be considered independently.

The macromolecular hub nucleus will generally be at least 10,000 molecular weight, usually at least 20,000 molecular weight, and preferably greater than 30,000 molecular weight. The maximum molecular weight can be indefinite, but below particulate size ($\leq 0.1\mu$), generally being under about 50,000,000, usually under about 2,000,000, and more usually under about 1,000,000, the preferred range being from about 20,000 to 2,000,000. The hub nucleus may be naturally occurring or synthetic, may be soluble or insoluble, cross linked or non-cross linked, and may have naturally available functional groups for linking or be modified by introduction of appropriate functionalities.

The hub nucleus will generally be of a size in the range of about 5 nm to 100$\mu$ more usually about 500 nm to 25$\mu$.

Of the various naturally occurring hub nuclei, the polysaccharides are of greatest interest, such as cellulose, amylose, agarose, sepharose, sephadex, dextran, amylopectin, and the like. For the most part, the polysaccharides may be substituted with amino- or carboxyalkyl groups or be activated with cyanogen bromide to provide sites for linking. The polysaccharides may be soluble or insoluble, preferably soluble.

A wide variety of synthetic polymers may be employed, both soluble and insoluble, such as acrylates, including acrylamides, polystyrenes, vinyl alcohols, ethers and esters, and combinations thereof, or the like. The synthetic polymers must have functionalities available for linking or such functionalities must be introduced. For example, polystyrene may be functionalized by introducing chloromethyl groups, carboxyl groups, or the like.

Besides the organic hub nuclei, inorganic hub nuclei may also be used, such as glasses, silicones, and the like.

While for the most part, carboxamido and amidino linkages will find application, other linking functionalities may also be employed, such as combinations of active ethylene and mercapto, phenol and diazo, active halogen and mercapto, disulfide, aldehyde and amino under reductive amination, and the like. The particular choice of the linking group to the support will depend upon the ease of preparation of supports having appropriate functionalization, the choice of the spacer arm, and the like. The bonding functionality is not critical to this invention, and various conventional or unconventional groups can be employed as desired although certain spacer arms and lengths are particularly preferred.

Either the support will have naturally occurring functionalities for bonding the spacer arm e.g. amino or oxy, or functionalities will be introduced e.g. with cyanogen bromide, or an activating compound will be employed e.g. carbodiimide with carboxylic acids. Where useful functionalities are not naturally present as part of the support, the length of the chain introduced for providing linking functionalities will generally be from about 1 to 5 atoms, usually from about 1 to 3 atoms.

The functionalities available on the support will be linked to spacer arms by any of a variety of stable covalent bonds. In addition to the functionalities of the spacer arm forming the covalent bond to the support and the chromogen, there will desirably be at least one other polar heteroatom in the spacer arm, usually chemically unreactive under the conditions of use, and generally not more than 10 polar atoms, more usually not more than 8 polar atoms, and preferably from about 1 to 6 polar atoms; and heteroatoms will normally be oxygen, nitrogen and sulfur, with chalcogens, oxygen and sulfur, normally bonded solely to carbon, either as oxy or non-oxy-carbonyl, including the sulfur analogs thereof, and nitrogen bonded solely to carbon and hydrogen, as amino or amido, normally secondary or tertiary amino, preferably tertiary amino. The chain may be aliphatic, alicyclic, aromatic or heterocyclic, or combinations thereof, where the heterocycles will normally be of from 5 to 6 members having from 1 to 3, usually 1 to 2 heteroatoms. The heteroatoms will normally be separated by at least 1 carbon atoms, and when bonded to saturated carbon atoms, at least 2 carbon atoms, except where the functionality naturally has heteroatoms joined to form stable covalent bonds. Various functionalities which may be present in the chain include amino, particularly tertiary amino, amido, oxygen and sulfur ether, sulfone, azo, and the like.

Usually, the spacer arm will have a length of about 5° A on the average and not more than about 30° A on the average, generally being from about 10° to 25° A on the average.

The spacer arm will normally have at least 1 atom in the chain, more usually at least 3 atoms in the chain, and generally not more than about 20 atoms in the chain, usually not more than about 16 atoms in the chain. As previously indicated, the atoms in the chain will be carbon, nitrogen, oxygen and sulfur, preferably carbon and nitrogen.

Illustrative spacer arms can be derived from polyalkylene polyamines, having from 2 to 5 nitrogen atoms, usually from 2 to 4 nitrogen atoms and alkylene groups of from 2 to 6 carbon atoms, more usually of from 2 to 3 carbon atoms; polyamides having from 1 to 5, usually from 1 to 4 amino acid groups of from 2 to 6, usually from 2 to 3 carbon atoms; combinations of dicarboxylic acids and diamines, wherein the acids are from 2 to 6 carbon atoms, more usually from 2 to 5 carbon atoms and the diamines are from 2 to 6 carbon atoms, usually from 2 to 4 carbon atoms; dicarboxylic acids of from 2 to 8 carbon atoms, usually of from 3 to 5 carbon atoms; alkylthiosuccinimidyl groups; and azo diaryl groups. The spacer arm will be chosen appropriately to link the functional group present on the support and a functional group available from the chromogen.

The chromogen will be chosen to either absorb light above 300 nm, usually above 350 nm, and preferably above 400 nm or fluoresce at wavelengths above 350 nm, preferably above 400 nm, and more preferably above 450 nm; to have a functional group for linking to the spacer arm or to allow for introduction of such a functionality; to have a hydroxyl group, normally phenolic; and upon cleavage of a glycosidyl bond to the phenolic oxygen, to undergo a substantial change in its spectroscopic properties. A wide variety of chromogens may be employed which have the aforementioned characteristics and properties. For the most part, the chromogens will be aromatic compounds having from 1 to 4 rings, which may be fused or non-fused and may have a wide variety of bathochromic functionalities which affect the spectroscopic properties of the compound.

The following is a list of illustrative compounds which can find use as the chromogen to be incorporated into the macromolecular substrate by bonding to the spacer arm and the saccharide (aldose or ketose).
p-carboxy-o-nitrophenol
p-nitro-m-carboxyphenol
4-amino-6-bromonaphthol-2
5-carboxyumbelliferone
2-naphthol-5-carboxylic acid
fluorescein isothiocyanate
4,5-dicarboxyfluorescein
2,6-dinitro-4-carboxyphenol
phenolphthalein isothiocyanate
5-carboxy-4',5'-dibromo-2',7'-dinitrofluorescein
5-hydroxy-3-carboxymethylindole
5-hydroxy-4-chloro-7-carboxyindole
5-carboxy-3-hydroxyindole
3-carboxyindophenol Of particular interest are nitrophenols, fluoresceins and 7-hydroxycoumarins.

The glycosides may be linked to the hydroxylic group in either the $\alpha$ or $\beta$ orientation. A wide variety of sugars, particularly monosaccharides, may be employed, such as galactose, glucose, mannose, acetylglucosamine, glucuronic acid, fucose, acetylgalactosamine, arabinofuranose, 6-phosphogalactose, and 6-phosphoglucose. The sugars may either have the D or L stereochemistry, normally having D.

The substrates may be employed with a wide variety of different enzymes, depending upon the particular sugar. The following is a list of enzymes of interest.

| I.U.B. Classification | Common Name |
|---|---|
| 3.2.1.20 | α-glucosidase |
| .21 | β-glucosidase |
| .22 | α-galactosidase |
| .23 | β-galactosodase |
| .24 | α-mannosidase |
| .25 | β-mannosidase |
| .29 | chitobiase |
| .30 | β-acetylglucosaminidase |
| .31 | β-glucuronidase |
| .38 | β-D-fucosidase |
| .49 | α-N-acetylgalactosaminidase |
| .51 | α-L-fucosidase |
| .55 | α-L-arabinofuranosidase |
| .bb | 6-phospho-β-D-galactosidase |
| .cc | 6-phospho-β-D-glucosidase |

Of particular interest are those enzymes of the IUB classification from 3.2.1.20 to 3.2.1.25, that is, glycosidases of 6 carbon sugars.

For the most part, the compounds of this invention will have the following formula:

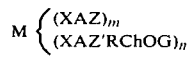

wherein:

M is the support, will be a suspendable particle in an aqueous medium, generally being of at least 10,000 molecular weight, more usually 20,000 molecular weight, and generally less than 50,000,000 molecular weight, more usually less than about 5,000,000 molecular weight, conveniently being from about 20,000 to 2,000,000 molecular weight; the support may be naturally derived, a modified naturally derived product, or a synthetic polymer, preferably being polyhydroxylic and more preferably polysaccharidic, either non-cross linked or cross linked, water soluble or insoluble, usually polyfunctionalized;

X is the functionality bonded to the backbone of the support and will normally be oxy, amino, or non-oxo-carboxyl, preferably oxy;

A may be taken together with Z to define H or with Z' to form a bond, but will normally be: an alkylene group of from 1 to 4, usually 1 to 2 carbon atoms, generally being more than 1 when joining 2 heteroatoms; or an alkylene carbonyl of from 2 to 8, usually 2 to 6 carbon atoms, e.g. methylene carbonyl group;

Z will normally be amino, carboxy, hydroxy, or Z'RH and may be halo, particularly α-halo, when A is alkylene carbonyl bonded at the carbonyl to X;

wherein the XAZ groups may be the same or different, normally being derived from a single precursor;

Z' is amino or non-oxo-carbonyl;

R is a spacer arm which is a bond or linking group of from about 1 to 20 carbon atoms, usually from about 1 to 16 carbon atoms, and preferably from about 4 to 16 carbon atoms, having from zero to 10, usually from 1 to 8 and preferably from 1 to 6, more preferably from about 2 to 4 heteroatoms which are chalcogen (oxygen and sulfur) bonded solely to carbon or nitrogen, nitrogen bonded solely to carbon and hydrogen, normally tertiary amino or amido; R does not include the functionality of the chromogen to which it is attached, but does include the atom attached to the functionality of the chromogen;

Ch is a divalent chromogenic group, bonded to a phenolic oxy group (ChO), has a chromophore which either absorbs light above 300 nm, usually above 350 nm, and preferably above 400 nm or is a fluorescer which emits light above 350 nm, preferably above 400 nm, and more preferably above 450 nm; and undergoes a substantial change in spectroscopic properties in going from glycosidyl substituted oxy to the unsubstituted compound, and has a functionality for bonding to R, usually non-oxo-carbonyl, amino, carbamyl, thiocarbamyl, mercapto and oxy; and G is a glycoside, either D, L or racemic, bonded in either the α or β orientation to the oxy oxygen of the chromogenic group;

n is at least one and will normally not be greater than the molecular weight of M divided by 2,000, usually not greater than the molecular weight of M divided by 5,000, and more usually not greater than about 500, frequently not greater than about 100, usually being at least 5, more usually at least 25; and m may be zero and up to 10 times the value of n, at the lower ranges of the values of n, usually not greater than five times n, more usually not greater than n.

A preferred group of macromolecular glycosidase substrates will have the following formula wherein:

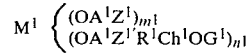

M¹ is a polysaccharide, either water soluble or insoluble, preferably soluble, either cross linked or non-cross linked, either naturally ocurring or synthetically modified, generally of at least 10,000 molecular weight, and usually not exceeding 10,000,000 molecular weight, more usually being in the range of about 20,000 to 5,000,000 molecular weight, conveniently in the range of about 30,000 to 2,000,000 molecular weight;

A¹ is alkylene of from 1 to 6 carbon atoms, usually from 1 to 4 carbon atoms, and preferably from 1 to 2 carbon atoms, there being at least 2 carbon atoms between heteroatoms or a carbonyl alkyl group of from 2 to 6 carbon atoms, usually of from 2 to 4 carbon atoms, with the carbonyl group forming an ester with the oxygen of the support;

Z¹ is amino, carboxy or Z¹'R'H; wherein the A¹Z¹ groups may be the same or different, normally being derived from a common precursor;

Z¹' is amino or non-oxo-carbonyl;

when Z¹' is amino, R¹ is poly(amino acid) of from 2 to 10 usually from 2 to 8, and preferably from about 4 to 6 carbon atoms, more preferably polyglycine or an alkylene di(non-oxo-carbonyl) of from 2 to 10, usually 2 to 8, and preferably 2 to 6 carbon atoms, bonded to Z¹' through an amide linkage;

Ch¹ is a divalent chromogenic group having a chromophore absorbing light at wavelengths greater than 300 nm, preferably greater than 350 nm, and more preferably greater than 400 nm and when a fluorescer, emitting light at wavelengths greater than 350 nm, preferably greater than 400 nm, and more preferably greater than 450 nm, generally of at least 6 carbon atoms and not greater than about 30 carbon atoms and bonded to oxy (Ch¹O) to form a phenolic group, which may be fused or non-fused to other rings, having from 1 to 4 rings, and may be substituted with oxo, cyano halo, particularly of atomic number 9 to 53, alkyl of from 1 to 6, more usually of from 1 to 4 carbon atoms, carboxyalkyl of from 1 to 6, more usually of from 1 to 4 carbon atoms, nitro, and alkoxy of from 1 to 4, more usually of from 1 to 2 carbon atoms; wherein the chromogen has a carboxy functionality, when R¹ terminates in an amino functionality, and an amino functionality, when R¹ terminates in a carboxy functionality, which are joined to form an amide linkage; and G¹ is a saccharide (glycoside) of from 5 to 8 carbon atoms, usually 6 carbon atoms, which includes glycoses (simple monosaccharides), glycosamines, N-acetyl glycosamines, glucuronic acids, and 6-phosphoglycoses, as open chain or furanosides and pyranosides;

n¹ is at least 1, and not greater than the molecular weight of M¹ divided by 150, usually divided by 250, preferably divided by 500, generally in the range of about 1 to $2 \times 10^4$, more usually in the range of about 50 to $5 \times 10^3$;

m¹ may vary from zero to the molecular weight of M¹ divided by 150, usually not more than the molecular weight of M¹ divided by 500, generally not greater than five times n¹, more usually not greater than n¹.

A preferred subgenus of the subject invention will have the following formula:

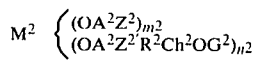

wherein:

M² is a polysaccharide, normally having 1, 4 or 1, 6 linkages, which may be soluble or insoluble in water, cross linked or non-cross linked;

A² is an alkylene group of from 1 to 4, usually 1 to 2 carbon atoms;

Z² is carboxy or Z²'R²H; wherein the A²Z² groups may be the same or different, but are normally derived from a common precursor;

Z²' is non-oxo-carbonyl;

R² is an alkylene polyamine having from 1 to 4 repeating units, wherein the alkylene groups are from 2 to 4, usually 2 to 3 carbon atoms, and where internal amine groups are linked by ethylene bridges or substituted by alkyl of from 1 to 3, usually 1 carbon atom;

Ch²O has a non-oxo-carbonyl functionality for joining to the terminal amino group of R² to form an amide and is of the formula:

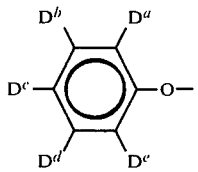

wherein:

two of the Ds of $D^{a-e}$ may be taken together to form a fused polycyclic structure with the ring to which they are attached, wherein the rings may be substituted or unsubstituted with oxo, oxy, amino, halo, cyano, alkyl, alkoxy of from 1 to 4 carbon atoms or the like; when no Ds are taken together, one of the Ds is non-oxy-carbonyl and the remaining Ds are hydrogen, nitro or halo of atomic number 9 to 53, usually 9 to 35. Included within the subject formula are Ar-hydroxycoumarins and fluoresceins, where the fluoresceins may be substituted by halo of atomic number 9 to 53, nitro, alkyl of from 1 to 6, more usually of from 1 to 3 carbon atoms, carboxy, carboxyalkyl of from 1 to 4, usually from 1 to 2 carbon atoms, and alkoxy of from 1 to 4, usually of from 1 to 2 carbon atoms, or combinations thereof, where substitution normally occurs in other than the 1',8'-positions (fluorescein-3',6'-dihydroxyspiro [isobenzo-furan-1(3 H)9'-[9 H]xanthen]-3-one);

G² will normally be a glycoside of from 5 to 6, usually 6 carbon atoms, particularly galactoside and glucoside;

n² will normally be in the range of about 1 to 2000, more usually in the range of about 50 to 500, while m² is in the range of about zero to 2000, usually in the range of about zero to 1500 and generally not greater than twice n².

The subject compositions are prepared by conventional means in accordance with the functionalities available on the support and which are avialable or introduced onto the chromogen. Appropriate spacer arms are chosen in accordance with the available functionalities. Amide bonds can be employed using carbodiimide activation of the carboxyl group, or with active esters, such as N-hydroxy succinimide; azo groups may be prepared by diazotization of an arylamino group; isothiocyanates may be linked to form thioureas in accordance with conventional procedures; active halogen may be substituted by alkoxide or mercaptide in accordance with known techniques; and amino linking groups may be provided by reductive amination of oxo-carbonyl with primary or secondary amines.

The subject compositions find a wide variety of application, where there is interest in detecting the presence of a glycosidase, particularly where it is desirable to modulate the signal in accordance with the steric requirements of the substrate. Illustrative of such a technique, is the imunoassay technique disclosed in U.S. Pat. application Ser. No. 964,099, filed Nov. 24, 1978. The description of that technique is incorporated herein by reference. Therefore, only limited details will be provided here.

The method provides conjugating a member of a specific binding pair, either antigen or antibody, to a porous particle. For use of the subject compositions, a glycosidase would be conjugated to the same or reciprocal member of the specific binding pair. By appropriate choice of additional reagents, the amount of enzyme bound to the particle would be related to the amount of analyte in the medium. The enzyme bound to the particle would be inhibited from acting on the macromolecular substrate of the subject invention. Therefore, the more of the enzyme bound to the particle, the lower the observed hydrolysis of the glycoside link. This technique is only illustrative of one of many possible techniques where a macromolecular substrate for a glycosidase is desirable for providing a signal.

The following examples are offered by way of illustration and not by way of limitation.

EXPERIMENTAL (All of the temperatures not otherwise indicated are in centigrade. All percents and parts are by weight, except for mixtures of liquids, which are by volume, unless otherwise indicated.) The following abreviations are employed:

ONPG-o-nitrophenyl-β-galactoside; HOAc—acetic acid; EDCl—ethyl dimethylaminopropyl carbodiimide; NHS—N-hydroxy succinimide; RSA—rabbit serum albumin.

EXAMPLE 1

Preparation Of conjugate Of o-nitrophenyl-$\beta$-galactoside and dextran with di(3-aminopropyl)piperazine spacer a. To 7 ml of 1.8 N Na chloroacetate solution and 3 ml water was added to 2 g dextran T2000 (pharmacia), followed by the addition of 10 ml 2.5 N aq. NaOH, and the mixture heated at 70°–75° for 1.5 hr and allowed to stand overnight. To the mixture was added 2 ml glac. HOAc and the mixture then dialyzed against 10 l. 5% aq. HOAc (4×24 hr) and then against deionized H$_2$O, 10 l. (4×24 hrs). By employing radioactivity labeled chloroacetate, it was found that there were about 1.21 $\mu$moles of carboxymethyl per mg of dextran.

b. To 80 ml of an aqueous solution containing 1.96 mmole of the carboxymethyldextran prepared above was added 8 ml (40 mmole) of N,N'-bis-(3-aminopropyl)piperazine and the solution adjusted to pH 4.75 with HCl, followed by adding 18 g (90 mmole) EDCl and allowing the solution to stand at R.T. for 24 hrs. The reaction mixture was then dialyzed against 12 l. deionized water containing 150 g K$_2$HPO$_4$ and 75 g KH$_2$PO$_4$ (4×25 hrs) and the number of amino groups determined by employing trinitrobenzenesulfonic acid was found to be 68% of the available carboxy groups.

c. To 10 ml DMF was added 387 mg 2-nitro-5-carboxyphenyl-$\beta$-galactoside, 249 mg EDCl and 151 mg N-hydroxy succinimide and the mixture stirred at R.T. for 1 hr. To 10 ml of aqueous solution containing the aminosubstituted dextran prepared above (9.2 mM in amino groups) was added 2.5 ml of the NHS ester prepared above and the reaction mixture stored at R.T. for 24 hrs. The reaction mixture was dialyzed against water (4×) and the product assayed for o-nitrophenyl-$\beta$-galactoside groups (ONPG). The product was found to be 7.0 mM/ml in ONPG groups by UV.

EXAMPLE 2

Preparation of conjugate of o-nitrophenyl-$\beta$-galactosidase and dextran with ethylene diamine and bis(3-aminopropyl) piperazine spacer To 5 ml of carboxymethyldextran solution, 48 mg/ml in dextran and 66 mM in acid groups (0.33 meq. of acid) was added 0.4 ml (6.0 mmoles) ethylenediamine. The solution was adjusted to pH 4.7–4.8 with conc. HCl and divided into 5 portions, numbered E1–E5. These were treated respectively with 40, 80, 120, 200, and 400 mg EDCl and stored at room temperature for 16 hrs.

Similarly, to 5 ml of a carboxymethyldextran solution having the same composition described above was added 1.3 ml (5.9 mmoles) bis(3-aminopropyl)-piperazine. The solution was adjusted to pH 4.7–4.8 with conc. HCl and divided into 5 portions, numbered P1–P5. These were treated respectively with 40, 80, 120, 200, and 400 mg of EDCl, and stored at room temperature for 16 hrs.

Solutions E1–E5 and P1–P5 were dialyzed 2× water, then 1×0.1 M phosphate, pH 7.5. The solutions were analyzed for primary amino groups and dextran, and the results are reported as meq amine/g dextran: E1–1.04, E2–1.08, E3–1.12, E4–1.05, E5–1.07; P1–0.30, P2–0.55, P3–0.35, P4–0.85, P5–0.93.

The various solutions E1–E5 and P1–P5 were diluted with 0.1 M phosphate buffer to equivalent dextran concentrations, roughly 15 mg/ml. One ml of each solution was treated with 0.5 ml of a 0.1 M solution in DMF of the NHS ester of 2-nitro-5-carboxyphenyl-$\beta$-galactoside. After storing at room temperature overnight, the various solutions were dialyzed 3×0.1 M phosphate buffer, pH 7.0. The solutions were assayed for dextran and ONPG moieties and the results reported as meq ONPG/g dextran: E1–0.85, E2;14 0.89, E3–0.87, E4–0.83, E5–0.87; P1–0.31, P2–0.45, P3–0.57, P4–0.85, P5–0.81.

The substrate activity was determined by combining an aliquot which had been diluted 1:11 with 0.5 ml of a solution made from 25 ml $\beta$-galactosidase and 6 ml .3 M phosphate, pH 7, with 0.07 M magnesium. The relative activities of the resulting materials as substrates for $\beta$-galactosidase were estimated to be: P5>P4>P3>E5>P2>,P1. No reaction was observed with E1–E4 over a 24 hr. period.

EXAMPLE 3

Conjugation of ONPG through triglycyl spacer arm to Affigel 102A

Into 2.5 ml DMF was disolved 173 mg of p-carboxy ONPG, 60 mg NHS and 114 mg EDCl and the mixture stored at room temperature for 1 hr. To an aqueous solution of 104 mg triglycine and 0.15 ml triethyl amine in 2.5 ml water was added the above NHS solution and the mixture allowed to stand for 1 hr at room temperature. The solvent was then evaporated in vacuo, chased with toluene, ethanol and methanol. The product was then purified by preparative chromatography using MeOH:CHCl$_3$:HOAc–50:50:2, with the product being removed from the silica gel with methanol.

The above procedure was repeated on a larger scale to yield a total of 285 mg of the desired product. The triglycine derivative of p-carboxy ONPG (10 mg, 20 $\mu$moles) 1 ml of Affigel 102-A (20 $\mu$mole ml) and 0.5 ml H$_2$O were mixed. EDCl (8 mg, 40 $\mu$moles) was added and after 1.5 hr. at room temperature, the gel was filtered and washed with 5–10 ml 0.1 M phosphate buffer, pH 7, giving an essentially colorless product. This material slowly turned yellow in the presence of $\beta$-galactosidase indicating hydrolysis of the glycoside linkage.

Into 0.5 ml DMF was introduced 17 mg of p-carboxy ONPG, 8 mg NHS and 15 mg EDCl, and the mixture allowed to stand for 1 hr. To 5 ml of 0.1 M dipotassium acid phosphate containing approximately 1.5 ml Affigel 102A suspension (20 $\mu$moles/ml) was added the above prepared ester and the mixture stirred overnight at room temperature. The mixture was then filtered and washed thoroughly with the phosphate buffer.

Aliquots were introduced into 4 vials and diluted with 0.1 M phosphate buffer. The 4 vials were then treated as follows: nothing added to the first vial; 1 $\mu$l of $\beta$-galactosidase added to the second vial; 1 $\mu$l $\beta$-galactosidase and 25 $\mu$l of an anti($\beta$-galactosidase serum added to the third vial and 1 $\mu$l of $\beta$-galactosidase plus 25 $\mu$l of a different anti($\beta$-galactosidase) added to the fourth vial, and then three drops added to all four of the vials of a tris/RSA/NaCl, pH 7.6 buffer and the solutions mixed. After standing overnight, some material had settled, with the settled material in vials 2 and 3 being clearly yellow, while the material in vials 1 and 4 being only slightly pale yellow.

The above test qualitatively shows that at least with one serum, $\beta$-galactosidase can be inhibited from reacting with the polymeric substrate by the presence of anti($\beta$-galactosidase).

EXAMPLE 4

Conjugation of HIgG and β-galactosidase

A reaction mixture was prepared by combining 4 ml HIgG (8.34 mg/ml, 50 mM phosphate buffer, pH 7.0), 2.17 ml phosphate buffer, pH 7.0, and 20 μl of a DMF solution of m-(N-maleimidyl) benzoic acid N-hydroxy succinimide ester (10 mg/ml) added with rapid stirring. After 30 min under $N_2$ at room temperature to the reaction was added 1 ml 1 M NaOAc to adjust the pH to 5. The mixture was then chromatographed on Sephadex G25-F (2.4×20 cm), eluted with 20 mM NaOAc, pH 5.0, containing 0.15 M NaCl at a rate of 30 ml/hr, collecting 6.6 ml fractions. Fractions 5-7 were pooled. Analysis by titration with cysteine showed about 7 maleimide groups per HIgG.

The maleimide modified HIgG was diluted with phosphate buffer followed by addition of 2 ml of a β-galactosidase solution in 50 mM phosphate buffer, pH 7.0 (0.67 mg/ml), to provide a final reaction volume of 14.1 ml. The following table indicates the various amounts of solutions added for three preparations.

| Conjugate | Maleimide HIgG ml | Maleimide HIgG mg | Phosphate Buffer, pH7 0.5M ml | Phosphate Buffer, pH7 0.05M ml |
|---|---|---|---|---|
| 1 | 1.5 | 2.54 | .15 | 10.45 |
| 2 | 5.0 | 8.45 | .50 | 7.60 |
| 3 | 11.85 | 20.03 | 1.25 | — |

The reaction was carried out at R.T. for 21 hrs under $N_2$. Any remaining maleimide groups were reacted with cysteine-HCl. The solutions were concentrated under $N_2$ with an Amicon Ultrafiltration cell over a PM30 membrane (conjugates 1 & 2), PM10 membrane (conjugate 3) to a final volume including wash of about 2 ml. The three samples were then chromatographed on Biogel A5M (82×1.5 cm) with PBS, 5 mM $NaN_3$, 1 mM $Mg(OAc)_2$, eluting at 4-8 ml/hr and collecting fractions of about 2.5 ml. With Conjugate 3 as exemplary, fractions 25 to 34 were pooled and assayed. Approximately 67% of the enzyme activity was recovered as conjugate product. Based on radioactive counting of radioactivity labeled HIgG, approximately 81% of the HIgG was recovered in total. The concentration of enzyme in the pool of conjugates was 31.45 μg/ml, while the concentration of HIgG was 83.4 μg/ml.

EXAMPLE 5

Preparation of rabbit anti(HIgG) (Ranti(HIgG)) conjugated to Sepharose 4B Beads Into a reaction vessel was introduced 2 ml containing 7.5 mg of rabbit anti(HIgG) in 0.1 M $NaHCO_3$, pH 8.1, 0.5 M NaCl and 0.9 CNBr activated Sepharose 4B beads and the mixture stirred at 4° for 6 hrs, followed by stirring at R.T. for 2 hrs. To the mixture was then added 0.1 volume 1 M 2-aminopropanol, pH 8.0 and the mixture stirred overnight at 4°. By employing radioactive Ranti(HIgG), it was found that 6.6 mg had coupled.

The beads (protein ~5 mg/ml packed beads) were washed by sequential suspension in 1×PBS (0.5 hr), and centrifugation (3×). After suspending the beads in twice their volume of PBS, 1.5 ml of the suspension was exposed to the small probe of a Sonicator (model W185 Systems, Ultrasonics Inc) at power 60 watts (setting ~1.5). The sample was cooled in an ice-bath and sonicated for 3 min, followed by centrifugation, resuspension and an additional 2 min sonication as above.

EXAMPLE 6

Conjugation of ONPG to Dextran T40 through N,N'-bis-(3-aminopropyl) piperazine A. 3-Hydroxy-4-nitrobenzoic acid (100.3 g, 95% pure, 0.53 mole) was added to methanol (1250 ml) to which had been added acetyl chloride (25 ml). The solid dissolved over a period of two days. After six days, the solution was filtered to remove undissolved impurities. The crude ester was obtained by evaporation of the solution. Several crops of crystals were taken, the last from a 50 ml volume. The combined crops were recrystalized from methanol (150 ml). Two crops of the ester as yellow-brown crystals, m.p. 89°-91°, (98.7 g, 0.50 mole) were obtained.

B. Acetobromogalactose (100.1 g, 95% pure, 0.23 mole) and methyl 3-hydroxy-4-nitrobenzoate (45.5 g, 0.23 mole) were dissolved in acetonitrile (600 ml). Silver oxide (30 g, 0.26 equiv.) was added to the stirred solution. The black solid gradually turned gray. After ten minutes, an additional portion of silver oxide (20 g, 0.17 equiv.) was added. Stirring was continued for an additional twenty minutes. The reaction mixture was filtered through a Celite pad to remove the silver salts. The filtrate was evaporated to give a crude brown crystaline mass (115 g). This material was recrystalized from ethanol (400 ml). Two crops of off-white crystals, m.p. 150°-152° (99.6 g, 0.19 mole, 83% yield) were obtained.

C. The tetracetate prepared above (B) (119 g, 0.226 mole) was added to methanol (1 l). The mixture was heated at 60° until the solid dissolved. Triethylamine (25 ml) was then added, and the solution was heated at 60° for an additional two hours. The crude solid product was obtained in several crops by evaporation of the solution, the final crop being taken from a 20 ml volume. The crude material was used in the next reaction without further purification.

D. The crude ester (prepared from 119 g of tetracetate in the preceding reaction) was added with stirring to 1 N NaOH (1.5 l.). After 15 min, the ester had dissolved and hydrolyzed. The solution was neutralized with concentrated HCl to give a cloudy orange solution, pH 7.5. The solution was clarified by filtration, then acidified with 1 N HCl (250 ml) to give a light yellow solution, pH 3-3.5. The resulting acid precipitated and was collected by filtration. It was washed with water (20 ml) and methanol (50 ml). The crude acid was recrystalized from methanol (900 ml), giving silky white needles (34.7 g). The aqueous mother liquors were concentrated to an 800 ml volume and acidified to pH 2. An additional amount of the crude acid was obtained which was recrystalized from methanol (150 ml) to give needles (7.7 g). The total yield of purified acid was 42.4 g (123 mmoles), m.p. 172°-174°.

E. 3-β-Galactosyloxy-4-nitrobenzoic Acid (55.2 g. 0.160 mole), N-hydroxysuccinimide (20 g, 0.174 mole), and EDCl (35 g, 0.183 mole) were dissolved in DMF (200 ml). After two hours, the reaction was completed by TLC, (10-20% $MeOH/CHCl_3$) and showed some minor impurities in addition to the desired compound. The solution was used without further treatment.

F. Dextran T40 (101 g) was dissolved in 1.25 M aqueous sodium chloroacetate (500 ml). A 2.5 M aqueous solution of sodium hydroxide (500 ml) was added. The solution was heated at 80°-85° for 3 hr.

The reaction mixture was allowed to cool. Ethanol (1 l.) was added slowly to the stirred reaction mixture. The dextran began to precipitate after 350 ml had been added. Additional ethanol (2 l.) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l.) was then added slowly until a permanent cloudiness appeared in the solution, then more rapidly. The gummy precipitate of the dextran was then allowed to settle out overnight.

G. Carboxymethylated dextran T40 (as a gum, prepared from 100 g dextran T40) was dissolved in water (250 ml). A solution of N,N'-bis-(3-aminopropyl)piperazine (400 g, 2.0 mole) in hydrochloric acid (680 g of 8.52 mmole/g, 5.80 mole) was added. To the resulting solution was added EDCl (201 g, 1.05 mole) in water (250 ml). The reaction was stored at room temperature for 22 hrs. At the end of this period, ethanol (3 l.) was added. The dextran began to precipitate afer 1.5 l. had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted in 1 l. and found to be 104 mM in amino broups by assay with trinitrobenzenesulfonic acid.

H. A solution of the aminodextran prepared above (G) (1 l. of 104 mM, 104 mmole) was treated with $K_2HPO_4$ (89 g, 0.5 mole) to give a solution buffered at pH 8–8.1. A DMF solution of the NHS ester (E) (160 mmole) was added slowly. The resulting solution was stored at room temperature for 24 hrs. The dextran was precipitated by the addition of ethanol (3 l.). Precipitation began after addition of 350 ml of the ethanol. The precipitate was allowed to settle out overnight.

The dextran was purified by two additional precipitations in the manner already described. The final gum was dissolved in water (1 l.). The solution was clarified by filtration first through a medium-porosity glass frit, and then through a 0.8 μMillipore filter.

The resulting solution was diluted to 1. A sample was diluted 1:121 and had $A_{320}=1.15$. Based on $E_{320}=2700$, the ONPG-group concentration was 52 mM.

The solution was preserved by addition of $NaN_3$ (0.65 g). To demonstrate the use of the subject compositions, the following assay was carried out.

The assay employed the following reagents:
Buffer: PBS, 0.1% RSA, 5 mM $NaN_3$, 0.1 mM $Mg(OAc)_2$
Particles: (Ex. 5) RantiHlgG in buffer at 0.2 ml/ml
Conjugate HlgG-(β-galactosidase): Ex. 4 in buffer at 9 μg β-galactosidase/ml
HlgG: 5.0 mg/ml in PBS, 5 mM $NaN_3$, further diluted as indicated
Substrate: (Ex. 1) ONPG-Dextran (2 M mol. wt.), 4 mM ONPG in PBS, 5 mM $NaN_3$ The protocol was as follows: combine each of 50 μl of the conjugate solution, 50 μl of HlgG solution and 50 μl of the particles with 100 μl of buffer and combine the diluted reagents in that order. Incubate at R.T. for 3 hrs. Add 0.1 ml substrate and 0.4 ml buffer and aspirate the mixture into a spectrophotometer cell and read the absorbance (420 nm) at 37° to 10 and 40 sec after adding the substrate. The following table indicates the results.

| Tube | Particles[1] | HlgG dilution[2] | Rate (min$^{-1}$) | Activity % |
|---|---|---|---|---|
| 1 | − | inf. | 0.776 | (100) |
| 2 | + | inf. | 0.186 | 24 |
| 3 | + | 16384 | 0.150 | 19 |
| 4 | + | 4096 | 0.196 | 25 |
| 5 | + | 1024 | 0.328 | 42 |
| 6 | + | 256 | 0.548 | 71 |
| 7 | + | 64 | 0.702 | 90 |
| 8 | + | 16 | 0.762 | 98 |
| 9 | + | 4 | 0.768 | 99 |
| 10 | + | 1 | 0.762 | 98 |

[1] − buffer; + particles
[2] Inf - HlgG solution substituted with buffer. HlgG solution serially diluted four-fold The above results demonstrate an assay for HlgG covering a concentration range of about 300 fold ranging from about 100 to 0.3 nM.

The subject compositions find a wide variety of applications, where steric inhibition of approach to a glycosidase is of interest. In addition, the subject compositions provide a high localized concentration of substrate, which can be readily observed by spectroscopic means or visible observation. The subject compositions are found to be quite active glycosidases, despite the size and presence of a macromolecule adjacent the enzyme labile bond. Thus, the subject compositions find use, where an enzyme is employed as a label, being particularly advantageous, where steric considerations are of interest. With the subject compositions, the effective molecular weight of the substrate can be widely varied as desired, so as to provide varying effects.

Although the foregoing invention has been described in some detail by way of illustration and example for purposes of clarity of understanding, it will be obvious that certain changes and modifications may be practiced within the scope of the appended claims.

What is claimed is:

1. A Compound of the formula:

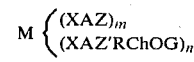

wherein:
M is a polysaccharide macromolecular support of at least about 10,000 molecular weight;
X is a functionality bonded to the backbone of said support and is oxy, amino or non-oxo-carbonyl;
A is alkylene of from about 1 to 6 carbon atoms or alkylenecarbonyl of from about 2 to 6 carbon atoms or is take together with Z to define H or with Z' to form a bond;
Z is amino, carboxy, hydroxy, Z'H or when A is alkylenecarbonyl, halo bonded to alkylene;
Z' is amino or non-oxo-carbonyl;
R is a bond or linking group of from 1 to 16 carbon atoms and from 1 to 8 heteroatoms which are chalcogen and nitrogen, wherein chalcogen is oxy, oxo and the sulfur analogs thereof and nitrogen is amino or amido;
ChO is a divalent chromogenic group which has a phenolic oxy group and has a chromophore which either absorbs light above 300 nm or fluoresces emitting light above 350 nm and has a substantial difference in its spectroscopic properties between the substituted and unsubstituted phenolic oxy group;
G is a glycoside of from about 5 to 6 carbon atoms;
n is at least 1 and not greater than the molecular weight of M divided by 150; and
m is in the range of about 0 to 10 times n.

2. A composition according to claim 1, wherein R is a polyamino acid or alkylene polyamine of from about 2 to 10 carbon atoms; and
n is in the range of about 5 to 100.

3. A compound according to claim 2, wherein R is an alkylene polyamine and said chromagenic group has a nitrophenyl group.

4. A compound of the formula:

$$M^1 \begin{Bmatrix} (OA^1Z^1)_{m1} \\ (OA^1Z^{1'}R^1Ch^1OG^1)_{n1} \end{Bmatrix}$$

wherein:
$M^1$ is a polysaccharide of from about 10,000 to 50,000,000 molecular weight
$A^1$ is alkylene of from 1 to 6 carbon atoms or alkylenecarbonyl of from 2 to 6 carbon atoms;
$Z^1$ is amino, carboxy or $Z^{1'}R^1H$;
$Z^{1'}$ is amino or non-oxo-carbonyl;
$R^1$ is a mono- or poly(amino acid) of a total of from 2 to 10 carbon atoms;
$Ch^1O$ is a divalent chromogenic group having a chromophore absorbing light at wavelengths greater than 300 nm and has a phenolic oxy group bonded to $G^1$ which is a glycoside of 6 carbon atoms;
$n^1$ is in the range of 1 to the molecular weight of $M^1$ divided by 500; and
$m^1$ is in the range of from 0 to 10 times $n^1$.

5. A compound according to claim 4, wherein said glycoside is galactoside.

6. A compound according to claim 4, wherein said glycoside is glucoside.

7. A compound according to claim 4, wherein $m^1$ plus $n^1$ is not greater than the molecular weight of $M^1$ divided by 1,000.

8. A compound of the formula:

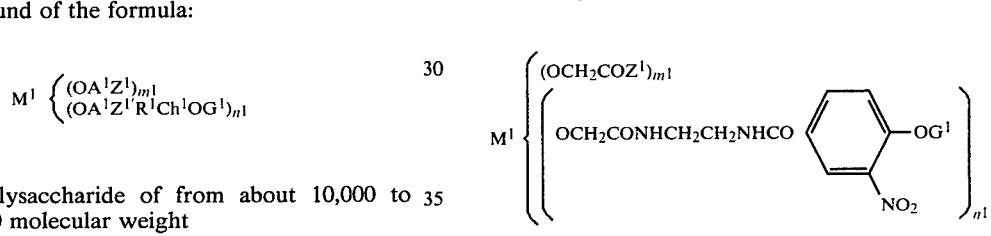

wherein:
$M^1$ is a polysaccharide of from about 10,000 to 10,000,000 molecular weight;
$Z^1$ is —OH or —NH(CH₂)₃N(CH₂CH₂)₂N(CH₂)₃NH₂;
$G^1$ is β-galactosidyl;
$n^1$ is on the average about 1 to the molecular weight of $M^1$ divided by 2,000; and
$m^1$ is on the average in the range of about 0 to equal to $n^1$.

9. A compound of the formula:

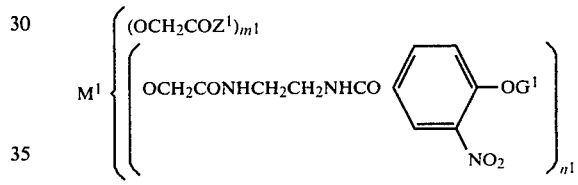

wherein:
$M^1$ is a polysaccharide of from about 10,000 to 10,000,000 molecular weight;
$Z^1$ is —OH or —CONHCH₂CH₂NH₂;
$G^1$ is β-galactosidyl;
$n^1$ is on the average about 1 to the molecular weight of $M^1$ divided by 2,000; and
$m^1$ is in the range of about 0 to equal to $n^1$.

10. A compound according to claim 1, wherein ChO is an aromatic compound having from one to four rings.

11. A compound according to claim 10, wherein R is a linking group having at least one nitrogen as a heteroatom.

* * * * *